United States Patent [19]

John

[11] 4,188,956
[45] Feb. 19, 1980

[54] METHOD FOR THE ANALYSIS, DISPLAY AND CLASSIFICATION OF MULTIVARIATE INDICES OF BRAIN FUNCTION—A FUNCTIONAL ELECTROPHYSIOLOGICAL BRAIN SCAN

[76] Inventor: E. Roy John, 930 Greacen La., Mamaroneck, N.Y. 10546

[21] Appl. No.: 918,730

[22] Filed: Jun. 26, 1978

[51] Int. Cl.$^2$ ............................................. A61B 5/04
[52] U.S. Cl. ................................................... 128/731
[58] Field of Search ........................... 128/2.1 B, 731

[56] References Cited

U.S. PATENT DOCUMENTS

| | | | |
|---|---|---|---|
| 3,498,287 | 3/1970 | Ertl | 128/2.1 B |
| 3,893,450 | 7/1975 | Ertl | 128/2.1 B |
| 4,094,307 | 6/1978 | Young, Jr. | 128/2.1 B |

OTHER PUBLICATIONS

Ueno et al., "Memoirs of the Faculty of Engineering Kyushu University, vol. 34, No. 3, Feb. 1975, pp. 195-209.

*Primary Examiner*—William E. Kamm
*Attorney, Agent, or Firm*—Eliot S. Gerber

[57] ABSTRACT

A method in electroencephalography (EEG) for the display of neurometric test data in which electrical activity generated by the brain either spontaneously or in response to specified challenges or conditions is detected at specified locations on the head surface of the subject by a plurality of electrodes. Features extracted from the spontaneous or evoked brain waves are quantified according to specified neurometric indices and categorized, using the mean values and standard deviations of control groups, according to their relative probability in a population of normal healthy people. Multivariate methods such as multiple analysis of variance or stepwise discriminate analysis can be used to identify independent features particularly useful for diagnosis. The values of such features can be used to construct a multivariate vector for each individual patient. If the length of this vector for data from a specified electrode placement is above the norm by a predetermined amount, for example, two standard errors, a plus sign is plotted at the corresponding position in a head diagram. If it is below the norm, for example, by more than two standard deviations ($p < 0.01$), a minus sign is plotted on the head diagram.

9 Claims, 4 Drawing Figures

METHOD FOR THE ANALYSIS, DISPLAY AND CLASSIFICATION OF MULTIVARIATE INDICES OF BRAIN FUNCTION—A FUNCTIONAL ELECTROPHYSIOLOGICAL BRAIN SCAN

BACKGROUND OF THE INVENTION

This invention relates to a method in electroencephalography (class 128, subclass 2.1B) for the compression, analysis, recording and display of brain wave data. More particularly, the present invention relates to neurometrics and to the display of quantitative features extracted from the spontaneous EEG or average sensory evoked responses (AER's). The evoked responses are generated by the brain in response to a series of standardized stimulus conditions or challenges, and then averaged in such a way as to obtain an estimate of the variance at every latency point in the analysis epoch.

Although the present invention is primarily applicable to medical sciences such as neuroscience, it may also be useful for the compression, analysis, recording and display of other variable data. The data reduction and display method of the present invention produces a symbolically coded display which is intuitively natural and is easily interpreted without extensive training. The present invention is particularly applicable to an intensive electrophysiological evaluation procedure (the neurometric examination) in which a subject has presented about one hundred specified conditions or challenges which can be considered as test items. The subject's brain waves may be analyzed to produce about 400 derived measures for each of 19 brain regions for each of these conditions. Accordingly, in this type of evaluation about a half million data values may be involved, which characterize the sensory, perceptual and cognitive processes of the subject.

At the present time, it is commonplace to observe a subject's brain waves by attaching a number of removable electrodes to the subject's scalp. The subject's electroencephalogram (EEG), at the present time, is generally recorded on a paper strip chart in analog form and analyzed, on a somewhat subjective basis, by visual inspection by a trained clinical electroencephalographer who is usually a neurologist.

Electroencephalography has long recognized the need for more objective criteria for EEG diagnosis and accordingly various numerical methods have been suggested to achieve a complete and objective analysis of brain waves. Among the factors which have been suggested to be considered are frequency distribution, voltage, locus of the phenomenon, wave form, interhemispheric coherence, character of wave form occurrence, regulation of voltage and frequency and reactivity.

Some systems have been suggested to use either high speed computer computation or special electronic circuits for characterizing the extracted data. However, one major deficiency in the art is the lack of an adequate and effective method of data representation which allows the user, for example, the physician, to easily interpret and classify the subject's responses.

Bickford et al in 1971, 1973 developed a technique which he called the Compressed Spectral Array (CSA) which represents the entire electroencephalograph (EEG) report as a picture which can be viewed on a single page. The CSA divides the EEG into 4 second intervals, separates the normal from the abnormal frequencies by spectral frequency analysis, and then superimposes the smoothed curves to yield a three-dimensional display which is a function of time and frequency. These reports may be found at *Electroencephalography & Clinical Neurophysiology*, 1971, page 632, and *Automation of Clinical Electroencephalography*, Raven Press 1973, pages 55–64. Although this method permits clear visualization, it does not provide for numerical or quantitative evaluation.

Gotman et al, in *Electroencephalography & Clinical Neurophysiology*, 1973, 35, pages 225–235, described that the weighted ratio of the activities in various frequency bands, when multiplied by a symmetry coefficient and summed, may provide an estimate of the subject's pathology. These results were displayed as "canonograms", which are polygons of multiple rings where the number of rings is proportional to the amount of slow waves in the record. The polygons are arranged in a topographic pattern which corresponds to electrode location on the head. While this method provides for a more quantitative analysis, it still fails to provide an unequivocal numerical index of abnormality.

U.S. Pat. No. 4,037,586 to Grichnik discloses a system for EEG display in which a console having a grid of lights indicates the particular order in which the electrodes are processed. The extracted data is displayed by pen recorders.

U.S. Pat. No. 3,707,147 to Sellers discloses a method for pictorial representation of physiological responses of the patient which vary with time and position. A series of line diagrams are generated on a cathode ray tube. The potential of the extracted signal is represented on the tube by the brightness of the lines on the tube, the vertical deflection of the lines or the spacing between consecutive lines.

SUMMARY OF THE INVENTION

The present invention provides for a topographic display which quantitatively evaluates and displays the degree of abnormality and is applicable to both electroencephalogram (EEG) and evoked potential (EP) analysis. The literature uses the terms "evoked potentials" or "evoked responses" interchangeably.

The invention provides a method of analysis and display of spontaneous activity and evoked responses generated by the brain and reactions to presented sensory conditions or challenges. These evoked responses reflect sensory, perceptual and cognitive processes and can be used to evaluate related functions in the brain.

According to the present invention a method for evoking, interpreting and displaying EEG and evoked brain responses comprises attaching a series of electrodes to the subject's head, presenting a specified challenge or condition to the subject, detecting the electrical brain wave activity representing the sensory, cognitive and perceptual responses of the brain, statistically analyzing the extracted data, and displaying the data on a sheet (hard copy) wherein each data symbol is associated with a particular topographical location on the subject's head and the size, density, nature (plus or minus) of the symbol is indicative of the quantitative degree of abnormality.

More particularly, a series of electrodes is attached to a subject's head. The subject is then exposed to a series of challenges or conditions. The brain, in response to the presented challenges or conditions, generates electrical waves which are detected by the electrodes. The specified challenges or conditions may be a series of visual flashes, auditory clicks or other sensory stimulation, including the absence of any of these.

The extracted data is statistically analyzed according to a systematic procedure. For example, EEG data are first analyzed, extracting specific neurometric induces such as the absolute and relative energy distributions, the distribution of frequencies in various banks, the energy ratio between bands, and the waveform symmetry. EP waveshapes may be analyzed to establish where significant changes occur when stimulus conditions are changed. Energies and latencies of such changes may be computed using normative data obtained from reference groups of healthy, well-functioning individuals, the neurometric features extracted from any individual being subjected to Z-transformation. That is, for each feature, the difference between the individual value and the healthy population mean is divided by the standard deviation of the healthy population. The effect of this transform is to provide the common metric of *relative probability* as the dimensions or units in which all features are stated. Relative probability here refers to the probability of obtaining the observed value by chance in a member of the healthy population. Since all neurometric features are thus stated in the same units, it becomes possible to construct a *multivariate abnormality vector, $\bar{Z}$*, for any combination of i features, where $\bar{Z} = \sqrt{Z_1^2 + Z_2^2 + Z_3^2 + \ldots + Z_i^2}$. The length of the vector $\bar{Z}$ reflects the extent of the individual abnormality in multivariate terms, while the orientation of $\bar{Z}$ reflects the nature of the abnormality. For any single neurometric feature or for any combination of multiple features, the value of $\bar{Z}$ is then topographically plotted according to electrode position in a symbolic code where (a) values within the normal range are plotted as two diagonal dots, (b) values above the normal range are indicated by a plus sign, (c) values below the normal range are indicated by a minus sign. Further, for values above and below the normal range, the size and density (darkness) of the symbol indicates the number of standard deviation units the particular value is from the normal (i.e., probability). As will be shown later, this plot allows the user to easily identify the degree of abnormality, the locus which generated the abnormality, the time at which the abnormality occurred, as well as the nature of the abnormality.

The computed $\bar{Z}$ vectors, in addition to being density coded, may also be plotted in n-space where one dimension exists for each discriminating index. Accordingly, an overall abnormality vector characterizing the subject may be constructed. Groups of subjects having vectors significantly closer together than the average distance between two points which might be expected by chance may be defined as a taxonomic class. Presumably, members of the same class will display similar symptoms caused by similar factors and/or will respond to similar treatments. Methods of numerical taxonomy, or mathematical pattern recognition, may be used to achieve objective classifications of such data vectors.

OBJECTIVES AND FEATURES OF THE INVENTION

It is a principal objective of the invention to provide a method for the analysis, compression, display and classification of neurological test data; a set of specified conditions or challenges are defined in which spontaneous and evoked electrical brain response data are obtained and neurometric features are extracted, transformed according to specified statistical procedures so as to indicate the difference of brain activity between the test subject and control groups of healthy, normally functioning people.

It is a feature of the present invention to provide for objective evaluation and compression of the data set, including use of the Z-transformation of statistical analysis. Treatment of neurometric data by multivariate techniques such as factor analysis, stepwise discriminant analysis, and multiple analysis of variance can provide indices which are similarly handled.

It is a further feature of the present invention to provide for hard copy (paper) display and recording in which data points from a specified electrode position which are a specified number of standard deviations above the norm are presented as plus signs in the corresponding location on a diagram of the head, data points a specified number of standard deviations below the norm are represented as minus signs, and data points within a specified number of standard deviations from the norm are represented as a pair of diagonal dots. The magnitude of the deviation of the individual measure from the norm for each head region is represented by the number, size and darkness (density) of the plus or minus signs entered in the corresponding portion of the head diagram.

The method of the present invention further includes the use of cluster analysis or mathematical pattern recognition techniques for the objective diagnostic classification of subjects according to the orientation of their $\bar{Z}$ or abnormality vector.

As a further feature, this method compensates for the large number of "false positive" responses expected by chance due to the large number of neurometric indices used. Indices describing disparate dimensions such as voltage, time, latency, coherence and symmetry are transformed to the common metric of relative probability. This enables comparison or combination of measures which were initially not dimensionally comparable. The approximate number of positive findings expected by chance can be calculated, and the density of points in any region of the measure space due to random positives can be estimated. Regions in which positive findings occur with a higher density than expected by chance can be identified by use of the F ratio from analysis of variance, comparing the average distance between points within such a region to the average distance between points expected by chance. In this fashion the statistical significance of the fact that an improbable number of individuals share an improbable pattern of significant findings can be estimated.

BRIEF DESCRIPTION OF THE DRAWINGS

Further objectives of the present invention, together with additional features contributing thereto and advantages accruing therefrom, will be apparent from the following description of one embodiment of the invention when read in conjunction with the accompanying drawings, wherein.

DESCRIPTION OF THE INVENTION

The invention provides a method for analysis and display of quantitative features extracted from the spontaneous and evoked electrical potentials generated by the brain in response to presented conditions and challenges. Those electrical potentials reflect brain functions which mediate the sensory, perceptual and cognitive processes of the subject and may be used to indicate the degree of normality of various brain regions with respect to such functions.

According to the present invention a method for evoking, interpreting and displaying the electrical brain responses comprises attaching a series of electrodes to the subject's scalp, presenting a specified challenge or condition, sensing the electrical brain activity related to sensory, cognitive and perceptual processes, extracting significant quantitative features from those data, statistically analyzing the extracted features according to a systematic procedure for estimating relative probabilities, representing the reduced data as a density coded symbolic display, and generating an overall uni- or multivariate vector characteristic of the subject for locating the subject within a defined taxonomic class.

Figure 1:
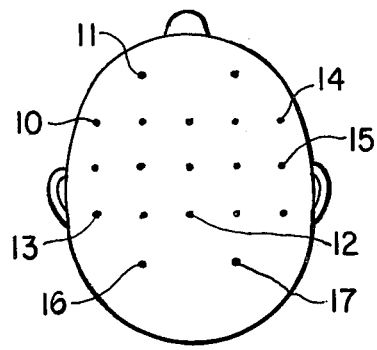
FIG. 1 is a top view of the head, with the front of the head toward the top of the page and the corresponding electrode placement pattern.

Referring now to FIG. 1, a series of electrodes is attached to the subject's head according to a uniform procedure which allows for comparable electrode positioning of heads of different dimensions. The preferred placement system is the Ten-Twenty Electrode System of the International Federation devised by H. S. Jasper (Electroencephalography and Clinical Neurophysiology, 1958). FIG. 1 is a top view of the head whose front faces the top of the page showing such electrode placement.

According to that system, a set of arcs of latitude and longitude are constructed along the surface of the approximately spherical cranium. Arc lengths from nasion to inion and from the left ear over vertex are measured. Electrodes are then positioned so as to divide each arc into six segments equal to 10%, 20%, 20%, 20%, 20% and 10% of the arc length. Using the points thus defined, additional arcs are located and electrodes are placed at particular intersections and positions along these arcs.

The electrodes are preferably attached with electrode paste as it is efficient and painless, although the electrodes may also be attached by subcutaneous needles or collodion. The scalp should be cleaned before paste application and an overall skin impedance of below 5,000Ω should be achieved to minimize noise. Next the subject is exposed to a series of challenges or conditions. Although the specific challenges or conditions may stimulate any of the senses, it is important that they be standardized to facilitate inter-subject comparison. In particular, visual and auditory conditions and challenges are particularly easy to consistently reproduce.

Important aspects of the sensory, cognitive and perceptual responses of the subject are reflected by electrical brain activity which is sensed by the attached electrodes. This sensed raw data is analyzed quantitatively according to selected criteria yielding extracted features of diagnostic value, called neurometric indices. Such indices are different for EEG and evoked response analyses.

Under each EEG condition, one minute of artifact-free activity is recorded as a series of five-second samples. Such artifact-free brain data may be selected according to the system and method of my copending application, "Prevention of Distortion of Brain Wave Data Due to Eye Movement or Other Artifacts," U.S. Pat. Ser. No. 873,119. After being edited to further eliminate artifacts, numerical indices for each derivation of each sample are computed.

The mean values and standard deviations are calculated for the full set of samples. The EEG indices include (i) absolute power in the low delta (0.5 to 1.5 Hertz), high delta (1.5 to 3.5 Hertz), alpha (7 to 13 Hertz), low beta (13 to 19 ) hertz, high beta (19 to 25) hertz, gamma (25 to 40), and total frequency (0.5–40 hertz) bands; (ii) relative power as a percentage in each frequency band; (iii) ratio of delta plus theta to alpha power; (iv) power symmetry within each frequency band between each pair of symmetrical (homologous) derivations; and (v) wave shape symmetry as assessed by cross-correlation of the total signals and by coherence within each frequency band between each pair of homologous derivations.

The evoked responses may be analyzed according to the system and methods disclosed in my book entitled "Neurometrics: Clinical Applications of Quantitative Electrophysiology", Lawrence Erlbaum Pub., 1977, see particularly pages 115–122, 211–222, 237,237, incorporated by reference herein. For each test condition, the AER of every derivation is computed from the evoked potentials yielding the digitized average signal voltage and its variance at each of 100 time points, samples at 10 msec. intervals across a one-second analysis epoch. The computed indices include (i) signal power, (ii) signal to noise ratio, (iv) mean squared first difference which is proportional to the product of the signal power and mean squared frequency; (v) difference in signal energy between homologous pairs; (vi) normalized difference in signal power between homologous pairs broken down into one term representing power asymmetry and one term representing waveshape asymmetry; (vii) cross-correlation coefficient; (viii) peak amplitude for each component; (ix) peak amplitude asymmetry, both absolute and relative for each component; and (xi) latency lag for each component. Each of these indices may be further specified by grouping the latency or time points where diagnostically discriminating reactions take place.

In one embodiment, over a half million data points are generated by this analysis due to the 92 challenges and conditions. 450 derived numerical indices and approximately 100 latency points. One method of data analysis uses analysis of variance, based on the F-ratio as defined by R. A. Fisher 1923 (Parl, B., Basic Statistics, pgs. 209–216)

$$F = \sigma 1^2 / \hat{\sigma 2^2}$$

$\sigma^2$ is the total deviation from the mean for a group of electrodes at a particular latency for the average responses computed in a particular latency for the average responses computed in a particular neurometric challenge or condition. $\sigma 1^2$ refers to the control group. $\sigma 2^2$ refers to the subject. $\hat{\sigma 2^2}$ is the variance, or the total deviation divided by the degrees of freedom. For a 19-electrode system with one mean value, there are 18 degrees of freedom.

This data analysis procedure has two steps. First the F-ratio, or ratio of the variance between the control and subject AER's for each latency point. For each index condition or challenge is computed for each electrode of the group of electrodes. The purpose of this first step is to decrease the amount of data which is subsequently processed. If the F-ratio is low, the data is eliminated. In effect, a low F-ratio for a subject indicates that his AER's for each challenge were about the same as the control group at each electrode. For each subject the deviation of the data value at each electrode from the mean data value of the group of electrodes is computed, that is $(X_i - \bar{X})_{i=1-19}$, where $X_i$ are the individual electrode AER values and $\bar{X}$ is the mean value of the AER's from the group of electrodes. Next the total variance of the AER's for that group of electrodes at a particular latency and index is computed:

$$\hat{\sigma}^2 = \sum_{i=1}^{19} (X_i - \bar{x})^2/18.$$

This calculation is performed for both the subject and control groups. The F-ratio is then calculated and the magnitude of the rato indices whether the subject and control data are homogeneous or alternatively whether the subject is significantly different from the control group. The magnitude of the R-ratio, which indicates significance of the difference, may be used to estimate the accuracy of diagnosis. For example, a specified value, for instance 0.01, would indicate that 5% of the time such results would occur by chance. Consequently, the critical F value will reflect the confidence level of the results.

A desirable second step in the data analysis is the reduction of the number of data points. This can be done on the basis of the F-ratio alone; for instance, disregard all data whose diagnostic significance does not meet a selected criterion (e.g., P<0.01). The remaining value will be the critical values.

However, the preferred method takes advantage of redundancy within the test items to permit a check between the F-value between comparable data from different tests. The data are regrouped according to similarity of test conditions, for example, the AER's from all checkerboard stimulus conditions, or all letter conditions, or all pattern conditions. This permits the selection of results which are robustly replicated. If within the group of similar conditions, similar F critical values occur at similar time points. Such values are considered particularly reliable and kept within the data set. Analyses such as this may reduce the number of data points by as much as a factor of 35, i.e., one-thirty-fifth the amount, and makes it possible to generate a readily comprehensible visual display. Alternative methode use principal component factor analysis or stepwise discriminant analysis to reduce the data set to the minimum discriminating dimensionality, and are described in the inventor's book *Neurometrics*.

The remaining values, after elimination of those having a low F ratio or which do not replicate robustly, are considered diagnostically reliable. These are analyzed according to the Z-transformation method (Parl, B., *Basic Statistics,* pages 165-166) which characterizes the deviation of the subject value from the control value as a number of standard deviations or "error steps".

The formula is:

$$Z = (X - M)/\sigma x$$

where the number of error steps, Z, is representative of a particular neurometric invariate or multivariate index and equal to the difference between the individual index value, for each electrode at each point in time, X, and the group mean value, M, divided by the standard deviation of the whole sample x. The total sample standard deviation is computed according to:

$$\sigma x = \sqrt{\Sigma(x - \bar{x})^2}$$

where x is the individual index value and $\bar{X}$ is the average index value of that group of one or more electrodes.

The Z computation characterizes the individual's index value as a number of error steps from the control value and indicates the relative probability that this value did not occur by chance. It is this Z value which is plotted in a topographical display according to whether it is (a) positive if it is greater than the control value, (b) negative if it is below the control value, (c) within the specified number of error units of the control value selected as the threshold for diagnosis. Each Z-transformed index value is plotted at a graphical location corresponding to the electrode location on the subject's head from which it was derived. The hard copy (paper coyp) display may be accomplished by a plotter instrument, such as electrostatic matrix printers, which are capable of representing data by dot densities up to 200 dots per inch. Z-values within a specified range of error steps of the control value are represented as two diagonal dots and values above and below the acceptable range are represented as a plus or a minus signal respectively, with the dot density proportional to the value of Z.

The number of signs, their size and darkness (density) is representative of the number of error steps a particular index value is from the control value. Multiple signs or very large and dark signs indicate significant deviation from the control value. Such a display will allow a skilled technician to easily interpret the topographical display and know whether the subject's responses were significantly different from those of the control group. Since the location of the entries on the head diagram corresponds to the anatomical location of the electrode at which the quantitative electrophysiological abnormality was found, since the neurometric test evaluates brain functions related to a wide range of capabilities, and since the density of the data entered on the head diagram is proportional to the deviation of the patient's brain function from the average value of a normal group represented as relative probability, such a series of head diagrams constitutes a Functional Electrophysiological Brain Scan.

Figure 2:
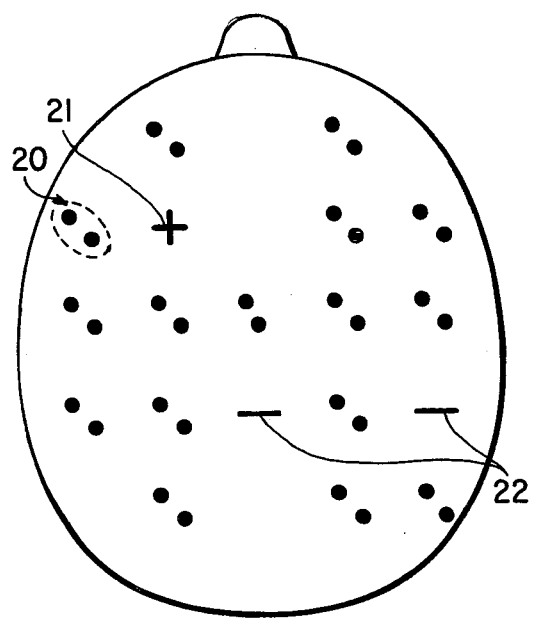
FIGS. 2 and 3 show a typical density coded Z-transformed display of neurometric indices extracted for various EEG and EP challenges and conditions.
Figure 3:
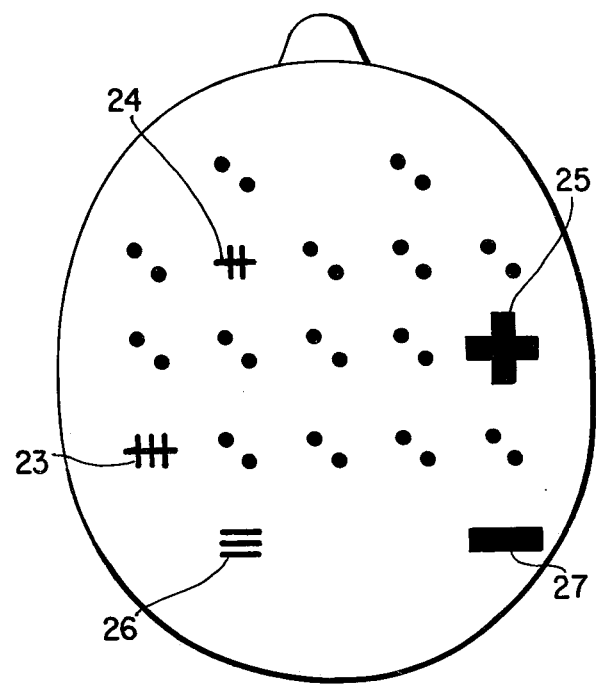
Figure 4:
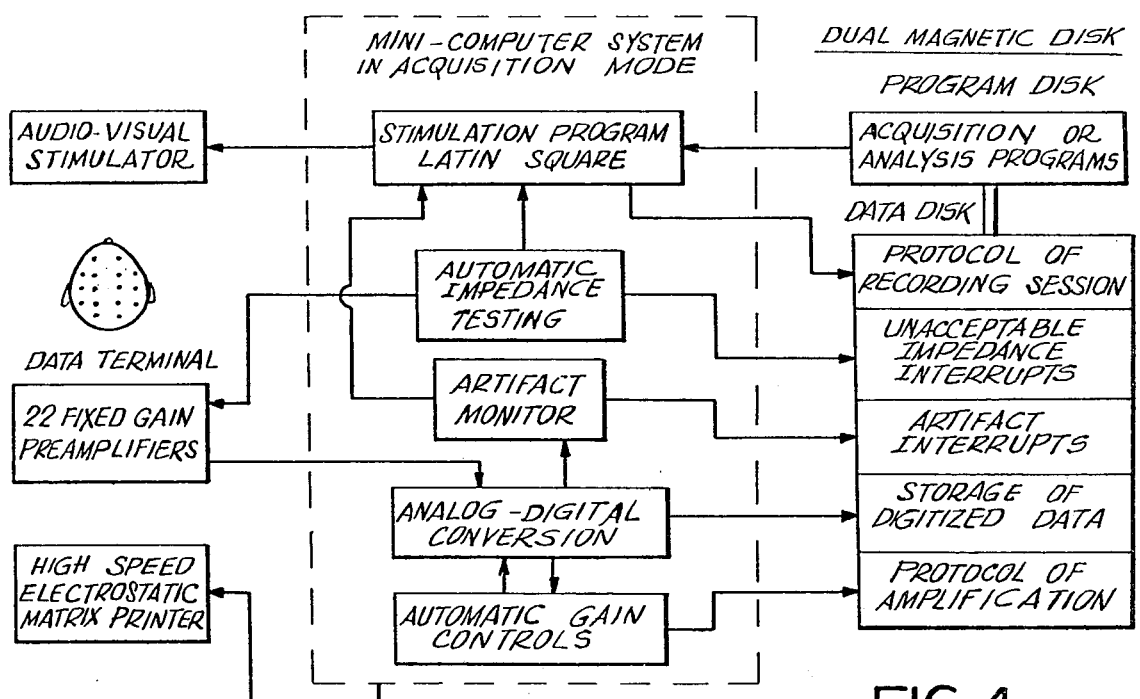
FIG. 4 is a block circuit diagram of a system which may be used according to the present invention.

As shown in the illustrative topographical display of FIG. 1, the two diagonal dot symbol 20 indicates the index value from the corresponding electrode 10 of FIG. 1 is within the specified number of error steps of the control value selected as the diagnostic threshold. In FIG. 2 the plus symbol 20 indicates this index value at this location, corresponding to electrode 11 of FIG. 1, is somewhat above the mean of the control range (P<0.05), while the minus symbols 22 show dots slightly below the control mean. In FIG. 3, a display showing the results of a different series of tests, the multiple plus signals 23,24 at locations corresponding to electrodes 13 and 11 of FIG. 1, indicate values significantly above the control mean (P<0.01, P<0.005), and the large dark plus symbol 25 indicates a value greatly above the control mean (P<0.001) at the electrode 15 of FIG. 1. In FIG. 3 the multiple minus signals 26 indicate values, at electrode 16 in FIG. 1, significantly below the control mean (P<0.005). In FIG. 3 the large minus sign 27 indicates an index value greatly below the control mean (P<0.001) at electrode 17 in FIG. 1. Values shown in FIG. 2 may be considered as not significantly different from the control group, whereas those of FIG. 3 indicate a deviation which is diagnostically significant.

Once having computed the Z-transform values, it becomes possible to objectively classify the subjects according to cluster analysis. A Z vector space is generated in which one dimension exists for the Z values of each index; the subject's individual Z index values are used to construct Z vectors. Accordingly, the orientation and length of those vectors are characteristic of the subject. The orientation defines the quality and the length the quantity of abnormality. Groups of individuals whose Z vectors are significantly close together, i.e., those whose average distance is significantly closer than the average distance between vectors representing the population as a whole (by an F ratio criterion) may be considered as members of the same objectively defined taxonomic class or "cluster".

The method of the present invention also compensates for false positive findings expected by chance. For all the indices, the probabilities of random positive findings are roughly equal. Given a population of normal subjects, one would expect the Z vectors representing such random findings to be randomly distributed throughout the "neurometric battery-dimensional" probability space. Using the distance matrix computation, one can determine the actual density of Z points in any domain of this space and compare it to the density expected by chance. Regions of high density reflect the improbable similarity of profiles of improbable values shared by a group, or cluster, of individuals. Presumably, these individuals share a similar set of brain dysfunctions; they constitute a potential diagnostic category. Membership in a particular cluster thus suggests a common etiology for the observed pattern of dysfunction and potentially provides a basis for the rational selection of differential treatment.

Although Z is here discussed only in the context of brain dysfunction, this concept can be generalized to problems in other fields and may provide the basis for a numerical taxonomic approach to the other areas of medical diagnosis.

What is claimed is:

1. A method for the acquisition, compression, analysis and display of neurometric test data which comprises
    connecting a plurality of electrically responsive terminals to the subject's scalp,
    exposing the subject to a specified set of conditions to evoke the subject's brain wave responses reflecting a variety of types of brain functions,
    sensing the subject's brain electrical responses,
    statistically analyzing said responses using a digital computer based system,
    representing the results of said statistical analysis as hard copy display according to a locational sign character convention in which the representation occurs at locations on the copy corresponding in format to the locations of said electrodes on the subject's head, and the deviations of said results above a statistically predetermined normal range of values are plotted as plus signs and values below the predetermined range of values are plotted as minus signs, with the size and density of the plotted symbols proportional to the statistical significance of such deviations.

2. A method as in claim 1 wherein values within the predetermined normal range are plotted as two diagonalized dots.

3. A method as in claim 1 wherein the data are statistically compressed by means selected from the group of F-ratio, multiple analysis of variance, factor analysis, and stepwise discriminant analysis.

4. A method as in claim 1 wherein the data is statistically evaluated by the Z-distribution.

5. A method as in claim 1 wherein values greatly above or below the predetermined range are encoded respectively as plus and minus signs whose size and density correspond in proportion to the significance of the deviation.

6. A method as in claim 1 and including the further steps of plotting the values for the subject across a set of conditions or challenges in multidimensional space to construct a vector indicative of the subject and grouping closely situated vectors together to define a taxonomic class when the distance between the vectors is less than the distance between individual vector points.

7. A method for the compression, analysis and display of neurometric test data which comprises
    connecting a plurality of electrically responsive terminals to the subject's scalp in a predetermined spacial format,
    sensing the subject's brain electrical activity,
    statistically analyzing said activity using a digital computer based system as compared to the activity of other subjects under similar conditions,
    representing the results of said statistical analysis as a hard copy display according to a locational sign character conventional in which the format resembles the head of the subject as seen from above and at a plurality of locations within said head-shape, the values of said results above a statistically determined range of values are plotted as plus signs and values below the statistically determined range of values are plotted as minus signs.

8. A method as in claim 1 wherein values within the predetermined range are plotted as two diagonalized dots.

9. A method as in claim 1 wherein the data are compressed by use of multivariate statistical procedures.

* * * * *